United States Patent [19]

Halleck

[11] 4,311,793
[45] Jan. 19, 1982

[54] STERILIZATION INDICATOR

[76] Inventor: Frank E. Halleck, 820 Elizabeth La., Erie, Pa. 16505

[21] Appl. No.: 159,781

[22] Filed: Jun. 16, 1980

Related U.S. Application Data

[63] Continuation of Ser. No. 898,306, Apr. 20, 1978, abandoned.

[51] Int. Cl.³ ............................................. C12Q 1/22
[52] U.S. Cl. ..................................... 435/31; 435/296; 435/299; 435/810
[58] Field of Search ................ 435/31, 287, 296, 805, 435/810, 299, 300, 301; 422/58; 116/207, 206, 216, 217; 73/358

[56] References Cited

U.S. PATENT DOCUMENTS

| | | | |
|---|---|---|---|
| 2,195,395 | 4/1940 | Chapman | 116/207 X |
| 2,854,384 | 9/1958 | Beakley et al. | 435/31 X |
| 2,998,306 | 8/1961 | Huyck et al. | 435/31 X |
| 3,114,349 | 12/1963 | Schuman | 116/207 X |
| 3,346,464 | 10/1967 | Ernst | 422/58 X |
| 3,440,144 | 4/1969 | Anderson | 435/31 |
| 3,568,627 | 3/1971 | Selinger et al. | 116/207 |
| 3,661,717 | 5/1972 | Nelson | 435/31 |
| 3,752,743 | 8/1973 | Henshilwood | 435/287 |
| 3,845,662 | 11/1974 | Surgina et al. | 73/358 |
| 3,980,581 | 9/1976 | Godsey, Jr. et al. | 116/207 X |

OTHER PUBLICATIONS

Smith & Underwood Salesmens' Catalog Sheet; 1961.

Primary Examiner—Robert J. Warden

[57] ABSTRACT

A sterilization indicator that yields immediate visual post sterilization evidence of attainment of sterilization parameters by the change of a chemical indicator and time verification of destruction of spores by subsequent culture and incubation of organisms.

17 Claims, 7 Drawing Figures

STERILIZATION INDICATOR

This is a continuation of application Ser. No. 898,306 filed Apr. 20, 1978 now abandoned.

GENERAL DESCRIPTION OF THE INVENTION

The invention relates to the development of a specialized sterilization indicator that yields post sterilization evidence of attainment of certain sterilization parameters by: (1) the charge of a chemical indicator to give immediate visual indication of achievement of the desired temperature, and (2) biological verification of the destruction of the spores contained therein by the subsequent incubation of these indicator organisms. The specification of the chemical indicator, or melt pellet in the sealed glass vial is such that the change takes place after achieving the desired sterilization temperature, i.e., 250 F. (121 C.), 270 F. (132 C.), or 285 F. (141 C.), for a defined period of time, thereby providing visual evidence of achieving sterilization temperature. The biological indicator ampule contains a growth promoting culture medium with a pH indicator or a vital dye selected for the indicator organism and spores of known heat resistance. Change of the pH indicator present in the culture medium and turbidity of the media following incubation are evidence for non-sterility, whereas no color change and lack of turbidity after incubation are evidence for sterility.

Two novel applications of this invention are as follows:

1. There are, at present, two generally known means for monitoring the efficacy of a solution sterilization cycle, neither of which is easily carried out. The first and most difficult would be seeding a solution to be sterilized with a known amount of spores, sterilizing the container of solution, recovery and concentration of the spores, and determination of the viability of the spores by various microbiological means. The second generally known method would be to fill a solution flask with culture medium, seed the media with spores of a known resistance, sterilize the container of medium and incubate the solution flask to determine viability of the spores following the sterilization cycle. This method has the disadvantages of requiring immediate use of the culture medium to preclude the growth of adventitious microorganisms and is costly due to the large quantities of culture medium which must be used for such tests. Storage of this type of test container also presents a problem in incubation due to their bulk.

This invention is applicable to monitoring sterilization of solutions by placement of the indicators directly in one or more of the containers of solution being sterilized. Usually one or more of the indicators is employed to monitor a solution sterilization cycle. It provides a compact and easy-to-use sterilization indicator which can be evaluated at the point of use, thereby eliminating the involved procedures and specialized equipment required in the commonly used methods described above.

2. There is presently no acceptable method for evaluating the efficacy of a washer-sterilizer cycle, due to the filling of the sterilizer with water, or water sprays, during a portion of the washer-sterilizer cycle. Such action does destroy the integrity of the packaging commonly used in spore strip type indicators, thus making them susceptible to post sterilization adventitious contamination and false sterilization test results. The system disclosed herein allows the retention of the stability of the biological and chemical indicator until the sterilization cycle is completed. Placement of this combined indicator may be accomplished by various means of anchorage, i.e., tape, clips, or implantation in goods.

Other prior art applications may also be applicable to such a combined and biological indicator system. Such applications might be placement in challenge packs or within other portions of a sterilizer load or such indicators may be used in the evaluation of a dry heat sterilization means.

REFERENCE TO PRIOR ART

U.S. Pat. No. 2,854,384 shows a glass ampule containing two compartments separated by an aperture partition. The aperture is closed by a meltable plug. One compartment contains spores and the other contains a culture media. During sterilization, the plug melts and falls into the culture media allowing the spores to enter the culture media for incubation.

U.S. Pat. No. 3,440,144 discloses an apparatus for testing sterilization including a bag containing a glass ampule with culture medium therein and a spore strip in the bag. After sterilization, the operator can break the glass ampule allowing the culture medium to join the spores for incubation.

U.S. Pat. No. 3,661,717 shows a unitary indicator much like the preceding indicator.

U.S. Pat. No. 2,998,306 shows a spore strip of a common variety.

None of the forementioned patents combine both an immediate visual indicator and the confirming biological sterilization indicator.

OBJECTS OF THE INVENTION

It is an object of the present invention to provide an improved sterilization indicator.

Another object of the invention is to provide a sterilization indicator that is simple and efficient to use.

Another object of the invention is to provide a self-contained indicator system, which is capable of being evaluated and incubated at the point of use, thus eliminating procedures requiring a laboratory and microbiologist.

Another object of the invention is to provide a sterilization indicator wherein a chemical indicator is isolated from culture media in a sealed glass ampule. The chemical indicator changes when the ambient media has reached a predetermined temperature level and the media containing spores can be subsequently incubated, thereby giving proof positive of the success of the sterilization cycle.

With the above and other objectives in view, the present invention consists of the combination and arrangement of parts hereinafter more fully described, illustrated in the accompanying drawing and more particularly pointed out in the appended claims, it being understood that changes may be made in the form, size, proportions and minor details of construction without departing from the spirit or sacrificing any of the advantages of the invention.

Construction of the indicator is not limited to the chemical indicator being located within the sealed ampule nor within the culture medium. Similar results may also be realized by placement of the chemical indicator externally, either separated or attached to the container of culture medium.

GENERAL DESCRIPTION OF THE DRAWINGS

DETAILED DESCRIPTION OF THE DRAWINGS

Figure 1:
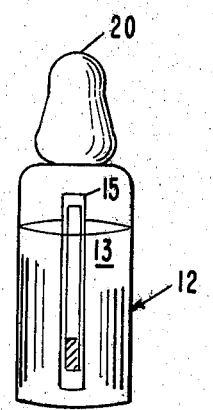
FIG. 1 is a side view of the sterilization indicator according to the invention.
Figure 3:
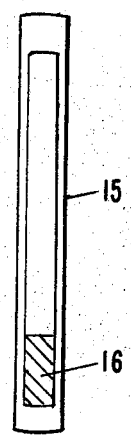
FIG. 3 is an enlarged view of the inner vial of the sterilization indicator showing the meltable pellet therein.
Figure 2:
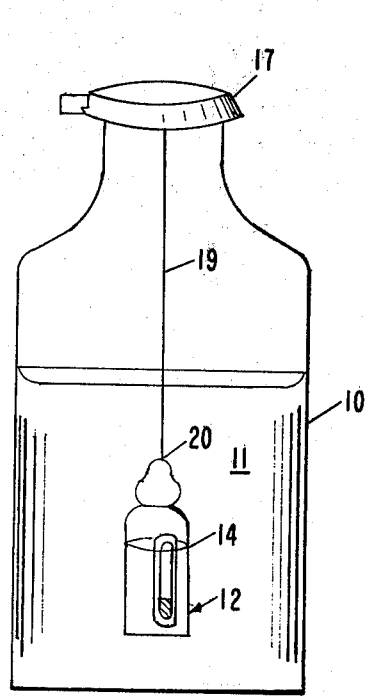
FIG. 2 is a view of the sterilization indicator in a container of solution to be sterilized.

Now, with more particular reference to the drawings and FIG. 2, the invention of the sterilizing indicator is supported in the container 10 which contains a solution 11 to be sterilized. The combination chemical and biological indicator 12 is suspended in the solution 11 by means of a cord 19 supported on the closed end 20 of the combination chemical and biological indicator 12 and attached to the cap 17 of the container.

The chemical and biological indicator 12 is made up of an ampule 14, which may be made of glass, sealed with an incubation medium 13 therein, which is a suitable broth that may contain an indicator. Examples of indicators are pH indicators such as phenol red or brom cresol purple or vital dyes, such as triphenyl tetrazolium chloride.

The inner tube 15 is hollow and contains a melt pellet 16. The melt pellet 16 is loosely received on the inside of the tube. The melt pellet 16 is adapted to melt at a predetermined temperature, for example, 250° F., 270° F. or 285° F. or at some suitable temperature. The broth, or incubation medium, 13 will also contain spores aerobic or anaerobic spore formers, or taken from the group of *Bacillus stearothermophilus, Clostridium sporogenes, Clostridium thermosacharolyticum, Bacillus subtilus*, and *Putrefactive anaerobe* 3679 of a predetermined variety, such as *B. stearothermophilus* or some other suitable spores taken from the group of *Bacillus stearothermophilus, Clostridium sporogenes, Clostridium thermosacharolyticum, Bacillus subtilus*, and *Purefactive anaerobe* 3679. The melt pellet 16 may be isolated since it may contain chemical materials that might be inhibitory to the spores or cidal to the bacterial growth and, therefore, interfere with the accuracy of the tests if they were not sealed up in the inner tube 15.

When the container 10 of solution to be sterilized is placed in a steam sterilizer or suitable thermal controlled chamber and brought up to temperature, and when the central part of the solution reaches a temperature at which the pellet 16 will melt, the pellet will melt and this will be visible from outside the container. If the melt pellet has not melted, the operator is immediately notified that the cycle was not successful and can resterilize the solution. Then, when the combination chemical and biological indicator 12 is removed from the container 10 and incubated, if the spores are viable, the vital dye will visually turn color and turbid. If a pH indicator is used, viable spores will also cause the solution to change color. If at the end of the incubation time, the spores are not viable, no change in clarity, no change in vital dye or color change will occur and a successful cycle is proven.

The biological test indicator could be used in a washer-sterilizer or other apparatus when it is desirable to get a preliminary indication of the success of a sterilizing cycle. If the pellet is melted, the operator knows immediately that the challenge part of the load has reached sterilizing temperature and can incubate the indicator to verify the success of the cycle. If the pellet is not melted, the load can immediately be resterilized.

Figure 4:
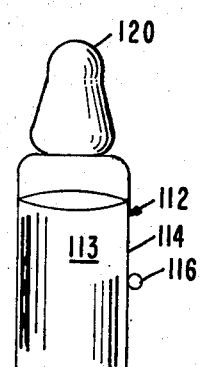
FIG. 4 is a view of another embodiment of the invention.

In the embodiment of the invention shown in FIG. 4, we show a biological indicator 112, which may be suspended in a solution, such as the solution 11 in FIG. 2. The chemical indicator 112 is made up of an ampule 114, which may be made of glass, sealed at 120 with an incubation medium 113 therein. This incubation medium may be a suitable broth that may contain an indicator. The indicator may be a pH indicator, triphenyl tetrazolium chloride or other suitable indicator. The melt pellet 116 is adapted to melt at a predetermined temperature, for example, 250° F., 270° F., or 285° F. indicating that such temperature has been reached. The broth or incubation medium 113 will contain spores of a suitable variety.

Figure 5:
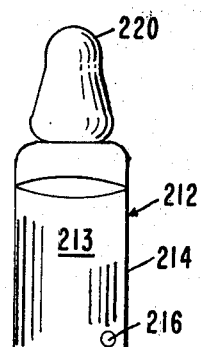
FIG. 5 is a view of yet another embodiment of the invention.

Referring to the embodiment of FIG. 5, this embodiment of the biological chemical indicator 212 has an upper closed end 220 and contains a broth or incubation medium 213 and a melt pellet 216 is supported inside the container 214.

Figure 6:
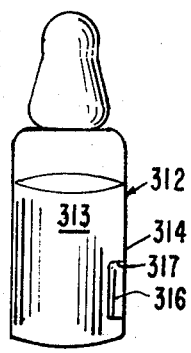
FIG. 6 is a view of another embodiment of the invention.

Referring to the embodiment of the invention of FIG. 6, the chemical biological indicator 312 shows a container 314 containing a broth 313 and having a suitable temperature indicating material 316 therein. This could be a filter paper with a temperature sensitive material painted onto it or it could be a material that melts at the preselected temperature. The enclosure 317 separates the material 316 from the broth 313.

Figure 7:
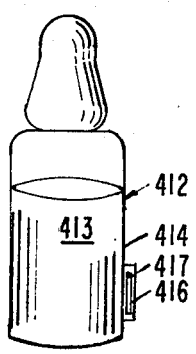
FIG. 7 is a view of another embodiment of the invention.

In the embodiment of the invention shown in FIG. 7, we show the chemical and biological indicator 412 containing the incubation medium 413 inside of the outer container 414. The container 416 is affixed to the outside surface of the container 414 and the temperature indicator 417 is housed in the container 416. When the temperature surrounding the container 414 reaches a predetermined temperature, the indicator material 417 will so indicate.

The foregoing specification sets forth the invention in its preferred, practical forms but the structure shown is capable of modification within a range of equivalents without departing from the invention which is to be understood is broadly novel as is commensurate with the appended claims.

The embodiments of the invention in which an exclusive property or privilege is claimed are defined as follows:

1. A sterilizing indicator comprising, a transparent container,
    said container containing a liquid culture medium containing viable spores,
    a temperature indicator,
    said temperature indicator being substantially surrounded in said liquid culture medium,
    said temperature indicator being adapted to change in appearance when it reaches a predetermined temperature to indicate whether the temperature has reached said predetermined temperature for a predetermined time, said culture media having indicating means to indicate whether viable spores are present therein when said culture media is incubated.

2. The sterilizing indicator recited in claim 1 wherein said indicating means comprises,
a pH indicator.

3. The sterilizing indicator recited in claim 1 wherein said indicating means comprises,
triphenyl tetrazolium chloride.

4. The sterilizing indicator recited in claim 1 wherein said viable spores comprise,
*Bacillus stearothermophilus.*

5. The sterilizing indicator recited in claim 1 wherein said viable spores comprise,
aerobic or anaerobic spore formers.

6. The sterilizing indicator recited in claim 1 wherein said viable spores are taken from the group of *Bacillus stearothermophilus, Clostridium sporogenes, Clostridium thermosacharolyticum, Bacillus subtilus,* or *Putrefactive anaerobe* 3679.

7. The sterilizing indicator recited in claim 1 wherein said temperature indicator is made up of a material that is non-toxic to said spores.

8. A sterilizing indicator comprising an outer transparent ampule,
said outer ampule containing a liquid culture medium containing living spores,
an inner ampule in said outer ampule,
said inner ampule containing a temperature indicator therein,
said inner ampule being sealed whereby said temperature indicator is isolated from said liquid culture medium, appearance at a predetermined temperature to indicate whether the temperature of said liquid medium inside said inner ampule and in said liquid medium has reached said predetermined temperature,
said liquid culture medium having indicating means therein to indicate whether viable spores are present therein when said culture medium is incubated after said outer ampule has been exposed to sterilizing conditions.

9. The sterilizing indicator recited in claim 1 wherein said indicating means comprises,
a pH indicator.

10. The sterilizing indicator recited in claim 8 wherein said viable spores comprise,
*Bacillus stearothermophilus.*

11. The sterilizing indicator recited in claim 8 wherein said viable spores comprise,
aerobic or anaerobic spore formers.

12. The sterilizing indicator recited in claim 8 wherein said viable spores are taken from the group of *Bacillus stearothermophilus, Clostridium sporogenes, Clostridium thermosacharolyticum, Bacillus subtilus,* and *Putrefactive anaerobe* 3679.

13. The sterilizing indicator recited in claim 8 wherein said inner ampule is supported in said culture media.

14. A method of testing a moist environment in a container to determine if a sterilizing procedure has been successful comprising,
placing in said container a transparent ampule containing a liquid culture media and spores in said culture media and a sealed tube containing a melt pellet in said culture media adapted to melt at a predetermined temperature,
exposing said container to sterilizing conditions of temperature and time,
if said pellet has melted, incubating said vial for a predetermined time whereby said liquid indicates that said spores have been killed and said procedure has been successful.

15. A method of testing a moist environment in a container to determine if a sterilizing procedure in said container has been successful comprising,
placing in said container an ampule containing a liquid culture medium and spores in said culture medium,
a temperature indicator disposed in said liquid culture medium adapted to change in appearance at a predetermined temperature in said container,
exposing said container to sterilizing conditions of temperature and time,
observing said temperature indicator and if said chemical indicator has changed, incubating said ampule for a predetermined time whereby said liquid indicates whether said spores have been killed and said procedure has been successful.

16. The method recited in claim 15 wherein said temperature indicator comprises,
a meltable pellet.

17. The method recited in claim 16 wherein said indicator is a pellet placed inside said ampule in said culture medium.

* * * * *

UNITED STATES PATENT AND TRADEMARK OFFICE
CERTIFICATE OF CORRECTION

PATENT NO. : 4,311,793

DATED : January 19, 1982

INVENTOR(S) : Frank E. Halleck

It is certified that error appears in the above—identified patent and that said Letters Patent is hereby corrected as shown below:

On the title page:

After the inventors name, the name of the - assignee - American Sterilizer Company, Erie, Pennsylvania - should appear.

Signed and Sealed this

First Day of June 1982

[SEAL]

*Attest:*

*Attesting Officer*

GERALD J. MOSSINGHOFF

*Commissioner of Patents and Trademarks*